United States Patent [19]

Coulson

[11] 4,381,298

[45] Apr. 26, 1983

[54] ORAL MALE CONTRACEPTIVE COMPOSITION

[76] Inventor: Patricia B. Coulson, 7417 Sheffield Dr., Knoxville, Tenn. 37919

[21] Appl. No.: 310,390

[22] Filed: Oct. 13, 1981

[51] Int. Cl.³ .............................................. A61K 31/56
[52] U.S. Cl. ................................................... 424/240
[58] Field of Search ......................................... 424/240

[56] References Cited

U.S. PATENT DOCUMENTS 4,094,977 6/1978 Seeger et al. ........................ 424/240
4,098,802 7/1978 Van der Vies ...................... 424/240

Primary Examiner—Elbert L. Roberts
Attorney, Agent, or Firm—Pitts, Ruderman & Kesterson

[57] ABSTRACT

A male contraceptive composition is described that may be administered orally. This permits adjusting the dose of the constituents to provide for sperm production inhibition and for normal functioning of secondary sex glands to permit normal sexual activity without fertility. The constituents of the composition are gossypol or derivatives thereof for controlling the sperm production combined with an orally active replacement androgen for counteracting the effect of the gossypol or its derivatives upon secondary sex glands. Ranges of composition and discussions of test results are described together with the method of determining the dose levels needed to achieve the desired result. The composition may be preferably administered as a pill. A maintenance dose level may be utilized after azoospermia sperm levels are achieved.

18 Claims, 4 Drawing Figures

GOSSYPOL

5α DIHYDRO-TESTOSTERONE      TESTOSTERONE      ANDROSTENEDIONE

FLUOXYMESTERONE
= 9α-FLUORO-11β-HYDROXY-
17α-METHYL-TESTOSTERONE

ORAL MALE CONTRACEPTIVE COMPOSITION

DESCRIPTION

1. Technical Field

This invention relates generally to compositions for inhibiting fertility in mammals and more particularly to an orally administered composition for substantially inhibiting sperm production in males without inhibiting any other sexual activity.

2. Background Art

An acceptable male contraceptive composition should satisfy the following criteria. Primarily, it should provide complete antifertility activity during treatment and be completely reversible after discontinuation of treatment. At the same time, it should not affect the secondary sex organs thereby permitting normal sexual performance such as erection, ejaculation, libido, etc. Also, the composition should be easily administered, such as orally, for convenience in use, and should cause no uncomfortable, bioligically significant or harmful long-term side effect.

To date, there are no oral male contraceptive treatments which are safe, reliable, and clinically or commercially available for males, i.e., approved by the United States Federal Drug Administration. Many compounds or medicines have been shown to cause the inhibition of sperm production (azoospermia) in experimental animals but many of these have either mutagenic or carcinogenic side effects. Others such as Danocrine must be given by injection, and will induce impotency along with the reduced sperm count.

A material that has been investigated as a contraceptive is gossypol, a phenolic binaphtalene compound. For example, published reports by the Chinese of gossypol activity indicated that the primary effect was an spermatogenesis in the seminiferous epithelium of the testes with no effect detectable on circulating hormone levels. However, recent research in the United States has demonstrated that gossypol in vivo (subcutaneously administered) will cause inhibition of the secondary sex organs in mice. In addition, it has been demonstrated that gossypol in vitro is capable of inhibiting the synthesis of testosterone in testes tissue and may be acting on specific dehydrogenase enzymes which are required for steroidogenesis. Other recent studies have shown that in the rat after 5 weeks of oral gossypol administration, serum testosterone and luteinizing hormone (LH) levels, but not follicle stimulating hormone (FSH) levels, are significantly decreased.

In still another study, an analogue of the luteinizing hormone releasing hormone (LHRH) was tested in males at concentrations two hundred times normal LHRH. This analogue may be administered via injections and nose drops, but not in pill form. Although significant decreases in sperm production were observed, a high incidence of impotency occurred due to the lowered blood levels of testosterone.

Accordingly, it is a principal object of the present invention to provide a contraceptive composition for complete antifertility activity during treatment with a complete return to fertility after discontinuation of treatment.

It is another object to provide a contaceptive composition to substantially inhibit the production of sperm but not inhibit any other sexual performance of the male.

It is also an object of the invention to provide a contraceptive composition that may be easily administrated as in pill form.

Another object of this invention is to provide a composition containing replacement support for any decrease in circulating or local testosterone hormone levels precipitated by the sperm-inhibiting component's effect on steroidogenesis or feedback regulation of the hypothalamic/pituitary axis.

It is a further object of the invention to allow utilization of the minimum effective dose of the components to insure infertility but provide potency.

Other objects and advantages of the invention will become apparent upon reading the detailed description with regard to the best mode for carrying out the invention.

DISCLOSURE OF THE INVENTION

In accordance with the invention gossypol or a derivative thereof, in the form of a pure substance or a biologically-acceptable acid or salt, is administered together with an orally active replacement androgen. The gossypol or its derivative substantially inhibits the production of sperm, and the androgen counters the gossypol-produced reduction in testosterone and thereby substantially prevents any change in the activity of the secondary sex glands. As used herein, the term "substantially inhibits" is to mean the reduction of the sperm production level to below that required for the fertilization of a female. This level is termed azoospermia. A quantity of 3–30 milligrams gossypol per kilogram body weight per day substantially inhibits sperm production, and a quantity of 1–5 milligrams per kilogram body weight per day of the replacement androgen maintains adequate sexual potency. A suitable orally active androgen is, for example, fluoxymesterone or medroxyprogesterone.

BEST MODE FOR CARRYING OUT THE INVENTION

Figure 1:
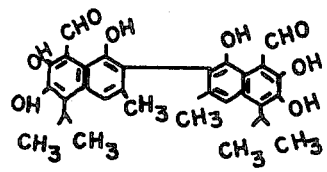
FIG. 1 is a drawing showing the basic binaphthalamine ring structure for gossypol, one of the phenolic binaphthalene compounds useful in the present invention.

Gossypol is a phenolic binaphthalene compound (1,1', 6,6', 7,7'-hexahydroxy-5,5'-diiso-prophyl-3,3' dimethyl (2,2'binaphthalene)-8,8'dicarboxy-aldehyde): it has the emperical formula $C_{30}H_{30}O_8$, F.W.=518.54. The basic binaphthalamine ring structure for gossypol is shown in FIG. 1. This represents the predominent form of a family of binaphthalene compounds found in plants such as cotton. It was originally isolated from oil extracts of the seeds, stems, or roots of the cottom plant (genus Gossypium). Gossypol is only one compound in a family or series of closely related binaphthalamine structures. Derivatives of gossypol may have varying degrees of antifertility properties and be equally effective in this invention. The isolated form or complex of this compund for administration can be free gossypol, gossypol aidehyde, gossypol hemicetal or gossypol guinoid. Free gossypol, gossypol acetate, gossypol acetic acid or gossypol formic acid are typical gossypol forms since all of these are active anti-fertility agents when taken orally. Other orally active gossypol acids and salts may be useful in the invention.

Figure 2:
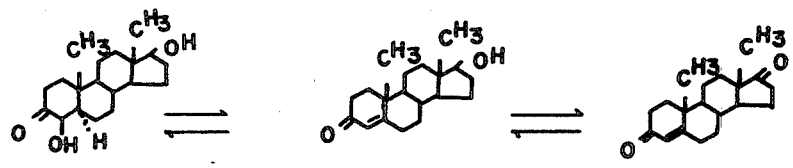
FIG. 2 is a drawing showing the chemical structures for dihydrotestosterone, testosterone and androstenedione, three of the most effective male androgen steroids found in the circulation and tissues.

The three most effective male androgen steriods found normally in the circulation and tissues in the human are dihydrotestosterone, testosterone, and androstenedione. The ring structures of these steroids are shown in FIG. 2. These are essential for the normal functioning of the male reproductive tract and interact specifically with the intracellular androgen receptor in the reproductive target tissues to control certain of the sexual activities, including potency. Of these, at least the testosterone production is adversely affected by the action of the gossypol. However, these particular compounds are not biologically active when taken orally in reasonable dose levels because of inactivation and poor absorption by the digestive tract. Thus, their replacement is not easily administered.

Figure 3:
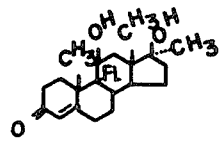
FIG. 3 is a drawing illustrating the chemical structure for fluoxymesterone, an androgen replacement compound useful in the present invention.

There are clinically proven androgen replacement compounds, however, which may be administered orally. One such compound, which is rather inexpensive to synthesize, is fluoxymesterone. The chemical structure of this compound is shown in FIG. 3. Other orally active androgenic compounds, such as medroxyprogesterone, are capable of interacting with the target reproductive accessory glands and their subcellular androgen receptors and may be equally as effective in this invention.

Experiments were performed to evaluate sperm levels and accessory reproductive glands in proven male BALB-C breeder mice (mean body weights of $31.3 \pm 5$ S.E.M., N=30) following 10 days of treatment with gossypol (subcutaneous injections of 10, 1, 0.1 or 0.01 mg/kg body weight) or with a combination of gossypol (1.0 mg/kg body weight) plus an androgen (medroxyprogesterone acetate; 1 mg/kg b.w.) compared to control animals injected with vehicle only. Details of the method of analysis are given in International J. of Andrology, No. 3, p. 507-518 (1980) which is hereby incorporated by reference. The results of these studies are plotted in FIG. 4.

Figure 4:
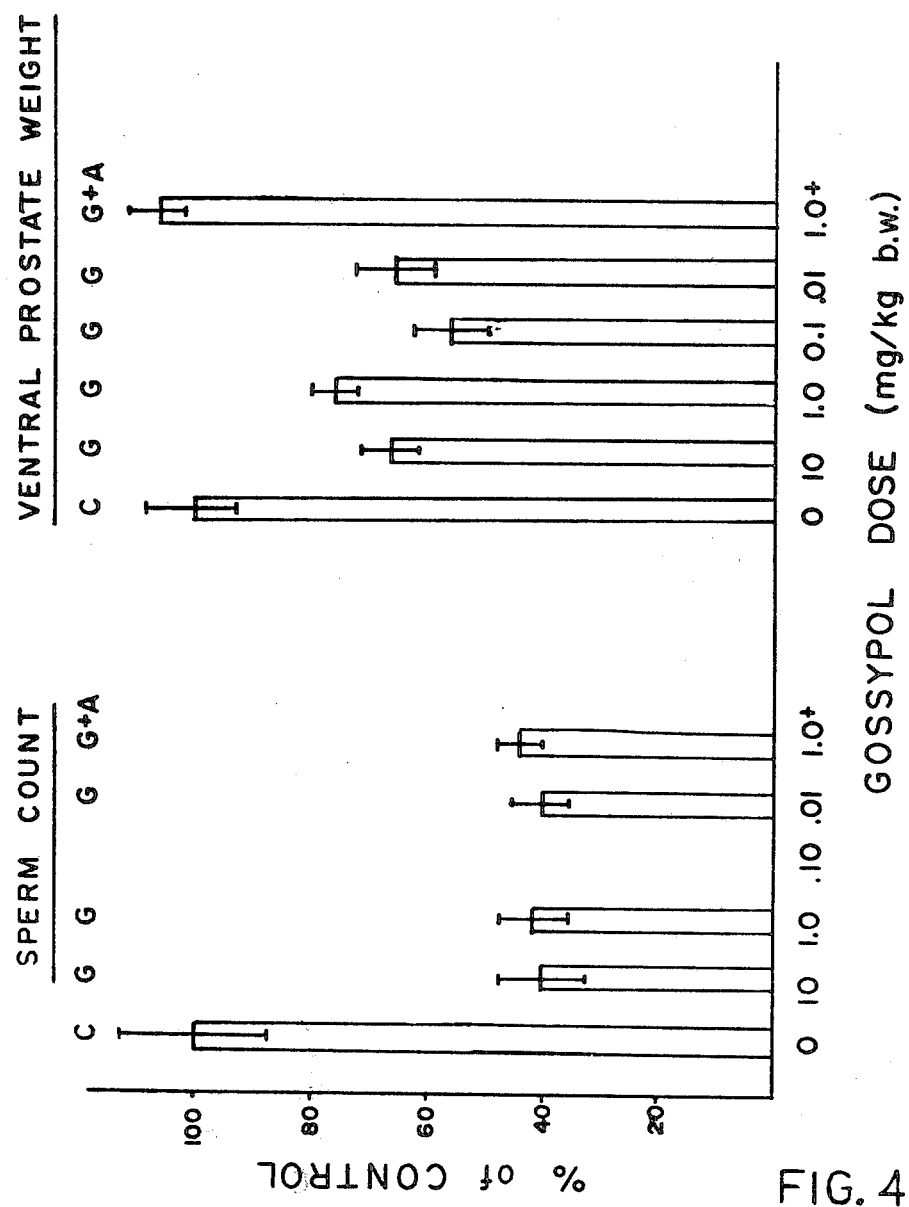
FIG. 4 is a graph of the test data showing results of treatment for the present invention as compared with controls and with only one component of the composition of the present invention.

As shown in FIG. 4, all groups of gossypol treated mice (G) had mean sperm counts reduced to less than 45% of control values, and the combination treatment mice receiving gossypol+androgen (G+A) showed a mean sperm count of 43% ($\pm 3$ S.E.M.) which was not significantly different from the gossypol treated groups. The ventral prostate wet weights were reduced to 55-75% of the control wet weights in all the gossypol treated mice (G), while the combination gossypol plus androgen treated mice (G+A) showed ventral prostate wet weights equivalent to or greater than those of control animals. The loss of ventral prostate wet weights from the gossypol treatment is and indication of the loss of activity of secondary sex organs leading to impotency, etc. Longer term treatments with combinations of gossypol and replacement androgens are needed to confirm that the sperm counts will continue to decrease while secondary sex gland activities are maintained.

In order to increase the effectivenss of the use of the composition of this invention, and to decrease the possibility of any occurrence of side effects or complications, it is advisable that the animal to receive contraceptive aide be given a thorough examination. It would be appropriate to obtain an ejaculation specimen, perform a sperm count, do a morphology study of the sperm and determine the ejaculation volume. Also a serum blood sample should be obtained in order to evaluate normal circulating levels of total testosterone, free testosterone, luteinizing hormone (=interstitial cell stimulating hormone) and follicle stimulating hormone. Following initial treatment with gossypol in the dosage range of 15-30 mg/kg/day plus a minimum level (e.g. 1 mg/kg/day) of an orally active androgen for 2 months, the patient animal be reexamined. This should include a sperm count, evaluation of the ejaculate, and an analysis of circulating testosterone hormone levels. If sufficiently low sperm levels have not been reached, a higher dose of gossypol in relation to body weight can be selected. When the sperm count is below the azzospermic level, the gossypol dosage may be reduced to a "maintenance" level, i.e., the minimum that will maintain the azoospermia condition. The level of the circulating testosterone will determine a needed increase or decrease to maintain other sexual performance for the animal. Periodic checks will ascertain the need for other adjustment of the dosage. Accordingly, a quantity of each of the constituents of the composition for a given animal are selected to substantially inhibit sperm generation as well as maintain effective performance of secondary sex organs.

The components of the contraceptive composition are easily prepared as powders, and thus the composition may be formulated into pills. Although they are generally insoluable in water, conventional methods can be used to formulate a suspension; thus, the composition may be administered as a liquid. Initial studies indicate that, while both components are required because of their mutual effect, they react with different sites. Accordingly, they may be administered separately to achieve the necessary dosage for a particular individual.

From the foregoing discussion, it will be recognized that an orally administered male contraceptive composition is provided that, in proper concentrations, substantially inhibits sperm production while substantially maintaining the circulating testosterone hormone levels required for proper performance of secondary sex organs.

I claim:

1. An orally active male animal contraceptive composition for substantially inhibiting sperm production without substantially affecting the activity of secondary sex organs during administration periods, which comprises:

a binaphthalamine structure compound selected from biologically acceptable gossypol and gossypol derivatives at a dosage sufficient for the substantial inhibition of sperm production to below the azoospermia level; and an orally active biologically acceptable replacement androgen at a dosage sufficient to inhibit a reduction of secondary sex organ activity by said binaphthalamine structure compound.

2. The contraceptive composition of claim 1 wherein said binaphthalamine structure compound is free gossypol.

3. The contraceptive composition of claim 1 wherein said biologically acceptable gossypol and gossypol derivative is an orally active gossypol acid or salt.

4. The contraceptive composition of claim 3 wherein said gossypol acid or salt is selected from the group consisting of gossypol aldehyde, gossypol hemiacetal or gossypol quinoid.

5. The contraceptive composition of claim 3 wherein said binaphthalamine structure compound is gossypol acetate.

6. The contraceptive composition of claim 3 wherein said binaphthalamine structure compound is gossypol acetic acid.

7. The contraceptive composition of claim 3 wherein said binaphthalamine structure compound is gossypol formic acid.

8. The contraceptive composition of claim 2 wherein said dosage of free gossypol is about 3 to 30 milligrams per kilogram body weight per day.

9. The contraceptive compound of claim 1 wherein said replacement androgen is selected from the group consisting of fluoxymesterone and medroxyprogesterone.

10. The contraceptive compound of claim 8 wherein said dosage of said replacement androgen is 1 to 5 milligrams per kilogram body weight per day.

11. An orally active male animal contraceptive composition for substantially inhibiting sperm production without substantially affecting the activity of secondary sex organs during administration periods, which comprises:
  a biologically acceptable and orally active form of gossypol in a dosage of 3-30 milligrams per kilogram body weight per day; and
  a biologically acceptable and orally active replacement androgen selected from the group consisting of fluoxymesterone and medroxyprogesterone in a dosage of 1 to 5 milligrams per kilogram per day.

12. A method of substantially inhibiting sperm production in male animals without substantially inhibiting the activity of secondary sex organs during administration periods, which comprises:
  orally administrating a biologically acceptable binaphthalamine structure compound selected from gossypol and gossypol derivatives at a dosage whereby said sperm production is substantially inhibited to below the azoospermia level; and
  orally administering a biologically acceptable orally active replacement androgen at a dosage whereby said activity of secondary sex organs is substantially unaffected by said gossypol and gossypol derivatives.

13. The method of claim 12 wherein said binaphthalamine structure compound is free gossypol and said replacement androgen is selected from fluoxymesterone and medroxyprogesterone.

14. The method of claim 13 wherein said free gossypol is about 3-30 milligrams per kilogram body weight, and said dosage of said replacement androgen is about 1-5 milligrams per kilogram body weight.

15. The method of claim 13 wherein said gossypol and said replacement androgen are administered separately.

16. The method of claim 13 wherein said gossypol and said replacement androgen are administered as a mixture.

17. The method of claims 15 or 16 wherein said gossypol and said replacement androgen are in liquid form.

18. The method of claims 15 or 16 wherein said gossypol and said replacement androgen are in solid form.

* * * * *